(12) United States Patent
Han (10) Patent No.: US 8,471,513 B2
(45) Date of Patent: Jun. 25, 2013

(54) RAIN SENSOR

(76) Inventor: Sea Yeoun Han, Incheon (KR)

( * ) Notice: Subject to any disclaimer, the term of this patent is extended or adjusted under 35 U.S.C. 154(b) by 238 days.

(21) Appl. No.: 12/988,428

(22) PCT Filed: Apr. 3, 2009

(86) PCT No.: PCT/KR2009/001739
§ 371 (c)(1),
(2), (4) Date: Oct. 18, 2010

(87) PCT Pub. No.: WO2009/131316
PCT Pub. Date: Oct. 29, 2009

(65) Prior Publication Data
US 2011/0031921 A1   Feb. 10, 2011

(30) Foreign Application Priority Data

Apr. 21, 2008 (KR) .......... 10-2008-0036853
Oct. 27, 2008 (KR) .......... 10-2008-0105209

(51) Int. Cl.
   *H02P 7/00*   (2006.01)
(52) U.S. Cl.
   USPC ........... 318/483; 318/643; 318/444; 318/480; 318/456; 250/573; 250/574; 250/227; 250/338.1; 250/208.1; 702/134; 702/132; 702/191; 356/445; 356/239.8; 340/602
(58) Field of Classification Search
   USPC .......... 318/643, 483, 444, 480, 456; 250/573, 250/574, 227.25, 338.1, 351, 208.1; 702/134, 702/132, 191; 356/445, 239.8; 340/602
   See application file for complete search history.

(56) References Cited

U.S. PATENT DOCUMENTS

| | | | |
|---|---|---|---|
| 6,118,383 A * | 9/2000 | Hegyi | 340/602 |
| 6,376,824 B1 | 4/2002 | Michenfelder | |
| 7,034,932 B2 * | 4/2006 | Kobayashi et al. | 356/239.8 |
| 7,050,949 B2 * | 5/2006 | Kokuryo et al. | 702/191 |

(Continued)

FOREIGN PATENT DOCUMENTS

| | | | |
|---|---|---|---|
| JP | 2005-233728 | | 9/2005 |
| JP | 2005233728 A | * | 9/2005 |
| JP | 2007-278711 | | 10/2007 |
| KR | 10-0751427 | | 8/2007 |

OTHER PUBLICATIONS

International Search Report—PCT/KR2009/001739 issued Dec. 18, 2009.

*Primary Examiner* — Walter Benson
*Assistant Examiner* — Jorge Carrasquillo
(74) *Attorney, Agent, or Firm* — Cantor Colburn LLP (57) ABSTRACT

During rain, including a light source (5) for radiating light such that the light is transmitted through a vehicle window (2), a light receiving element (6) for sensing an optical signal when the light radiated from the light source (5) is reflected from the raindrop fallen on the vehicle window (2) and performing a photoelectric transduction, and a receiver (9) for receiving the photoelectrically transduced signal from the light receiving element (6) and judging the level of rainfall. The light source (5) and the light receiving element (6) are inclined with respect to the surface of the vehicle window (2) such that the light of the light source (5) directly reflected from the vehicle window (2) exits to the outside of the light receiving element (6) and the light reflected from a raindrop (8) on the vehicle window (2) is received by the light receiving element (6) to operate a vehicle wiper.

16 Claims, 4 Drawing Sheets cross-sectional view

U.S. PATENT DOCUMENTS

| | | | |
|---|---|---|---|
| 7,235,944 B2 * | 6/2007 | Morishita | 318/483 |
| 7,348,586 B2 * | 3/2008 | Ishikawa et al. | 250/573 |
| 7,612,356 B2 * | 11/2009 | Utida et al. | 250/573 |
| 7,718,943 B2 * | 5/2010 | Johnson et al. | 250/208.1 |
| 2002/0047087 A1 * | 4/2002 | Schofield et al. | 250/208.1 |
| 2005/0178954 A1 | 8/2005 | Yukawa | |

* cited by examiner

FIG. 1 installation view

FIG. 2 cross-sectional view

FIG. 3 cross-sectional view

FIG. 4 installation view

FIG. 5 sensor substrate layout

FIG. 6

FIG. 7 conceptual illustration of a signal sensing process conceptual illustration of an ambient light reduction method

RAIN SENSOR

TECHNICAL FIELD

This invention relates to a rain sensor attached to a windshield for determining the level of rainfall by receiving the amount of the light reflected towards the light source from the raindrops fallen on the windshield on which the sensor is attached.

This invention further relates to a raindrop sensor immune to ambient light except the optical signal reflected from the raindrops, thereby enhancing the sensing efficiency of the level of rainfall.

BACKGROUND ART

Up to date, conventional rain sensors have been using the methods of: injecting an optical signal into the windshield to determine the level of rainfall by detecting the decrease in the amount of guided light through the windshield reaching the light receiving element attached to the opposite side of the light source when the raindrops fall on the windshield; transmitting a slanting signal light into the windshield to determine the level of rainfall by detecting the change in the amount of light reaching the light receiving element attached to the opposite side of the light source due to the change in the reflectance when the raindrops fall on the windshield; and attaching serially arranged rain sensors to the windshield to determine the level of rainfall by receiving the light reflected back towards the light source when the raindrops fall on the windshield where the sensors are attached. Among the above described methods, the first method requires a complicated optical system and brings on difficulties in mounting since the optical coupler must be in close contact with the windshield and maintain precise incident angle when the sensing signal light is transmitted into the windshield so as to be guided inside thereof. In the second method, the signal-to-noise ratio (hereinafter referred to as "SNR") is degraded because the light receiving element receives not only the reflected light from the raindrops bus also the light reflected from the surface of the windshield since the light receiving element is installed in the opposite side of the light source of the sensor. Disadvantage of the third method is a narrow and small sensing area for a light source and light receiving element set since it requires many light source and light receiving element sets to detect raindrops falling on a wide area due to the serial arrangement of the light source and light receiving element.

In summary, a conventional rain sensing method using internal light guiding phenomenon inside of the windshield requires a complicated optical system and brings on difficulties in mounting; in a method measuring reflecting light from the raindrops wherein the light source and the light receiving element are located apart opposing each other, the SNR is degraded due to the reflection from the surface of the windshield; a reflection type method wherein a light source and a light receiving element are serially arranged, has a narrow and small raindrop sensing area.

A pair of wipers is installed on a windshield to overcome a hindrance to visibility caused by rain during rain, and the intermittent speed control of the wipers is accomplished in a step-by-step manner according to the level of rainfall. Since the speed control system for such wipers provides only a couple of steps, it is impossible for a driver to operate the wipers at a desired speed corresponding to the level of rainfall.

Even in the products developed to solve above described problems, the SNR is degraded due to the large amount of reflection from the windshield in addition to the optical signal reflected from the raindrops therefore expected performance in sensing efficiency cannot be achieved.

Furthermore, in a conventional method, optical signals caused by the alternating motion of the wipers are also being received; hence the sensing efficiency is getting worse since it is affected by headlights from another person's vehicle. In other words, during the operation of the wipers headlights from another person's vehicle could be received in addition to the reflected light from the raindrops thereby causing malfunction etc.

SUMMARY OF INVENTION

Technical Problem

An objective of this invention, designed to solve above mentioned problems, is to provide a rain sensing method that is capable of sensing raindrops efficiently over a wide area using smaller number of light sources and light receiving elements in a reflective type rain sensing method, and easy to install due to its simplified optical system, and capable of minimizing the effect of ambient light by using a modulated light source, and not affected by the reflected light from the surface of the windshield, and efficient in rain sensing when viewing from an area standpoint.

Another objective of this invention, designed to solve above mentioned problems, is to provide a novel rain sensor having a simplified optical system for an easy installment, and capable of preventing degradation in the SNR affected by the light reflected from the surface of the windshield except from the raindrops by installing the light source transmitting light into the windshield and the light receiving element collecting reflected light from the raindrops inclined with respect to the surface of the windshield, and designed to exclude optical signals caused by the alternating motion of the wipers so that the effect from the headlights of another person's vehicle during the operation of the wipers is prevented so as to enhance operation reliability significantly.

Solution to Problem

To achieve above mentioned objectives, a rain sensor of the present invention having lattice-like arrangement pattern and reduced ambient light effect is characterized in that: it is comprised of a light source (5) radiating signal light according to the generated signal in a transmitter (11); a light receiving element (6), located in a unit sensing area and arranged with surrounding four light sources (5), for receiving light and facing towards the reflected light from the raindrops caused by the radiated light of the light sources (5); an infrared filter installed in the opening formed at the one side of the housing (1) of the rain sensor; and a receiver (9) excluding noise components caused by the reflection from the surface of the windshield (2) and extracting only the modulated frequency component of the optical signal to determine the amount of existing raindrops on the surface of the windshield so as to minimize the effect of ambient light and enhance the raindrop sensing probability;

the sensing area can be expanded by adding two light sources (5) and one light receiving element (6) in a lattice-like pattern to the left-right or top-bottom side of the unit sensing area comprising a light receiving element (6) surrounded by four light sources (5) for receiving light and facing towards the reflected light from the raindrops caused by the radiated light of the light sources (5);

the light sources (5) are infrared LEDs and arranged with the light receiving element (6) in a lattice-like pattern;

the interior of the housing (1) of the rain sensor is colored black to absorb light and surface-treated for diffuse reflection;

the transmitter (11) is comprised of an oscillator (13) oscillating a square wave between 10 KHz and 100 KHz frequency range and a modulator (14) modulating the infrared LED light source (5) according to the oscillated signal;

the receiver (9) is comprised of an amplifier (15) amplifying the photoelectrically transduced electrical signal from the light receiving element (6) and a band pass filter (16) filtering out frequency components identical to the oscillating frequency of the oscillator (13);

the infrared filter installed on the front surface of the light receiving element (6) suppresses reception of external visible light frequencies except the optical signal;

the receiver (9) transfers information to a microcomputer (10) according to the amplitude of the optical signal, then the microcomputer (10) determines the appropriate operation frequency of the wipers according to the pre-inputted look-up table and outputs a raindrop sensing signal (12).

According to the first feature of the present invention, in order to reduce sensing error of the rain sensor, a wide raindrop falling area was detected and the light sources and the receiving elements were arranged in a lattice-like pattern; and in order to prevent the effect of the light reflected from the surface of the windshield, the sensor substrate on which the light sources and the light receiving elements were attached in a lattice-like pattern was attached inclining with respect to the surface of the windshield. At this time, an optical signal, modulated with a specific frequency and radiated from the light source, is reflected from the raindrops and entered the light receiving element located in the lattice; then the received optical signal is transduced into an optical signal, and only the specific frequency used for the modulation is filtered out so as to minimize the effect of ambient light; and the demodulated signal is compared with the pre-inputted look-up table in the microcomputer, then a wiper operation signal is generated in accordance with the received signal.

To achieve above mentioned objectives, a rain sensor of the present invention is comprised of: a light source (5) radiating light into the windshield (2); a light receiving element (6) performing photoelectric transduction by sensing the optical signal when the radiated light from the light source (5) is reflected from the raindrops fallen on the windshield (2); and a receiver (9) judging the level of rainfall by receiving the photoelectrically transduced signal of the light receiving element (6), wherein the light source (5) and the light receiving element (6) are inclined with respect to the surface of the windshield (2) such that the light from the light source (5) that is directly reflected from the surface of the windshield (2) exits outside of the light receiving element (6), and only the reflected light from the raindrops fallen on the windshield (2) is received so as to operate the wipers.

It is characterized in that the light source (5) and the light receiving element (6) are mounted on the substrate (4), and the substrate (4) is inclined with respect to the surface of the windshield (2) such that the light source (5) and the light receiving element (6) are inclined with respect to the surface of the windshield (2);

the light receiving elements (6) are mounted on the central area of the substrate (4) at the outer area of the light receiving elements (6);

the housing (1) is installed on the windshield (2) where the light of the light source (5) is being radiated so that the front opening (3) and the windshield are facing each other, and the substrate (4) where the light sources (5) and the light receiving elements (6) are mounted is installed inside of the housing (1), and the substrate (4) where the light sources (5) and the light receiving elements (6) are mounted is installed inclining with respect to the windshield (2).

It is characterized in that the light source (5) is comprised of an infrared LED and the light receiving element (6) is comprised of an infrared sensor.

It is further characterized in that a plurality of light sources (5) is arranged at the top, bottom, left, and right side of the light receiving element (6) in a lattice-like pattern;

the sensing area can be expanded by disposing two additional light sources (5) and one light receiving element (6) at the top-bottom or left-right direction of a unit sensing area where a plurality of light sources (5) are disposed at the top, bottom, left, and right side of the receiving element (6) in a lattice-like pattern.

Advantageous Effects of Invention

Unlike a sensing method using the windshield as an optical waveguide or a method where a light source emitting signal light and a light receiving element are arranged to face each other, or a method where the a light source and a light receiving element are disposed serially along the same direction, a rain sensing method of the present invention has an adequate effect on reducing the probability of malfunctioning of the rain sensor by increasing the raindrop sensing probability where the light emitting light sources are disposed the receiving element so that the raindrops fallen on the surface of the windshield can be monitored over a wide area.

According to the present invention, a novel rain sensor having a simplified optical system for an easy installment, and capable of preventing degradation in the SNR affected by the light reflected from the surface of the windshield except from the raindrops by installing the light source transmitting light into the windshield and the light receiving element collecting reflected light from the raindrops inclined with respect to the surface of the windshield, and designed to exclude optical signals caused by the alternating motion of the wipers so that the effect from the headlights of another person's vehicle during the operation of the wipers is prevented so as to enhance operation reliability significantly can be provided.

BEST MODE FOR CARRYING OUT THE INVENTION

A rain sensor comprising a light source (5) radiating signal light according to the generated signal in a transmitter (11), a light receiving element (6) for receiving light in the unit sensing area facing towards the light reflected from the raindrops by the radiating light of the light source (5) and arranged with surrounding four light sources (5), an infrared filter installed in the opening formed at the one side of the housing (1) of the rain sensor, and a receiver (9) excluding noise components caused by the reflection from the surface of the windshield (2) and extracting only the modulated frequency component of the signal light to determine the amount of existing raindrops on the surface of the windshield so as to minimize the effect of ambient light and enhance the raindrop sensing probability is provided.

According to the present invention, a rain sensor comprising a light source (5) radiating light into the windshield (2); a light receiving element (6) performing photoelectric transduction by sensing the signal light when the radiated light from the light source (5) is reflected from the raindrops fallen on the windshield (2); a receiver (9) judging the level of rainfall by receiving the photoelectrically transduced signal of the light receiving element (6) are inclined with respect to the surface of the windshield (2) such that the light from the light source (5) that is directly reflected from the surface of the windshield (2) exits outside of the light receiving element (6), only the reflected light from the raindrops fallen on the windshield (2) is received so as to operate the wipers; and characterized in that the light source (5) and the light receiving element (6) are mounted on the substrate (4), and the substrate (4) is inclined with respect to the surface of the windshield (2) such that the light source (5) and the light receiving element (6) are inclined with respect to the surface of the windshield (2), is provided.

[Description of Embodiments]

Figure 1:
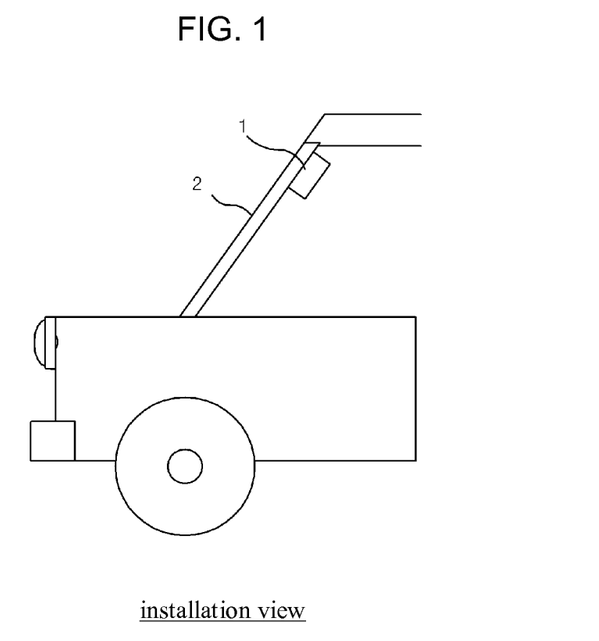
FIG. 1 is a conceptual illustration showing a rain sensor of the present invention installed on the windshield.
Figure 7:
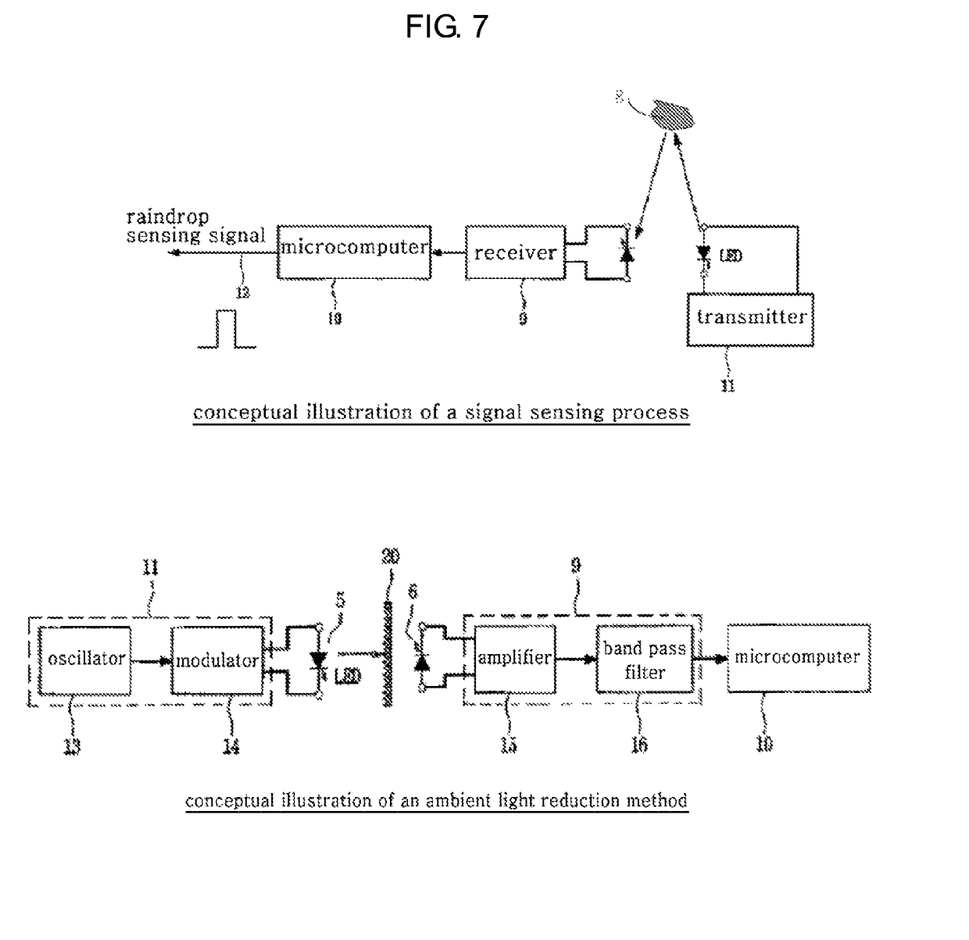
FIG. 7 shows a conceptual illustration of a signal sensing process and an ambient light reduction method of the present invention.

FIG. 1 is a conceptual illustration showing a rain sensor in accordance with the present invention, and a method of attaching a sensing substrate on the windshield inclining with respect to the windshield as light sources and light receiving elements are attached in a lattice-like pattern on the substrate. FIG. 7 is a conceptual illustration showing a method for an ambient light reduction inside of the sensor.

Figure 3:
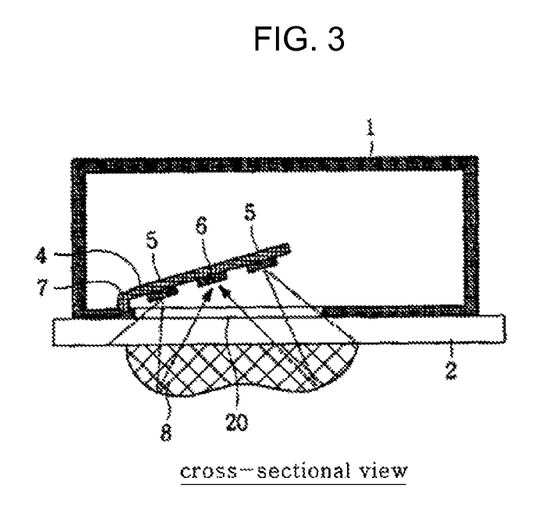
FIG. 3 is a conceptual illustration showing the light reflection process of the light source, which is a major element of the present invention, at a raindrop.

Referring to FIG. 3, reference number 1 represents the housing of a rain sensor of the present invention, reference number 2 represents a windshield, reference number 4 represents a lattice substrate where the light sources and the light receiving element are arranged in a lattice-like pattern and attached, reference number 5 represents an LED used as a light source, reference number 6 represents a light receiving element for transducing a received signal light into an electrical signal, reference number 7 represents a bracket for securing the lattice substrate, and reference number 8 represents a raindrop fallen on the surface of the windshield.

In the above described configuration, an infrared signal light radiated from the LED used as a light source passes through the infrared filter and the windshield (2) and some part of the signal light is reflected back from the raindrop (8) fallen on the windshield (2) and again passes through the windshield (2) and the infrared band pass filter and photoelectrically transduced in the light receiving element (6) which is located in the same direction as the LED in the light source (5). The photoelectrically transduced electrical signal is reformed as a signal in the receiver, and a wiper operation signal corresponding to the received signal is generated by comparing with the pre-inputted look-up table. At this time, since one light receiving element (6) is surrounded by four LEDs that are used as light sources in the configuration of the first unit sensing area therefore one light receiving element (6) can include four light paths, hence it is economical in terms of required number of light receiving elements. Moreover, since same effect of using four LEDs as in the first unit sensing area can be achieved by adding two LEDs and one light receiving element (6) to a neighboring sensing area, it has an advantage in that the number of elements can be reduced while expanding sensing area.

Meanwhile, referring to FIG. 7, reference number 9 represents a receiver, reference number 10 represents a microcomputer, reference number 11 represents a transmitter, reference number 12 represents a raindrop sensing signal for operating the wipers, reference number 13 represents an oscillator generating oscillation frequency for modulation of the light source, reference number 14 represents a modulator, reference number 15 represents an amplifier for amplifying the photoelectrically transduced signal in the light receiving element, and reference number 16 represents a band pass filter which extracts only the frequency components identical to the modulation frequency used in the transmitter among the frequencies included in the amplifier output In the above configuration, a square wave between 10 kHz and 100 kHz is oscillated by the oscillator (13), and the LED is optically modulated by the modulator (14) according to the oscillation signal. This generated optical signal is reflected from the raindrop (8) fallen on the windshield (2) and passes through the infrared filter and received by the light receiving element (6). The infrared filter has an effect which suppresses reception of external visible light except the infrared signal light. Photoelectrically transduced electrical signal from the light receiving element is amplified in the amplifier (15) and only the frequency components identical to the oscillation frequency of the oscillator (13) are filtered out in the band pass filter (16). Thus using the above described method most of the effect of the external light can be blocked except the signal light. A correct operation frequency of the wiper is determined in the microcomputer using the pre-inputted look-up table according to the amplitude of the generated signal light and the result is outputted.

Figure 2:
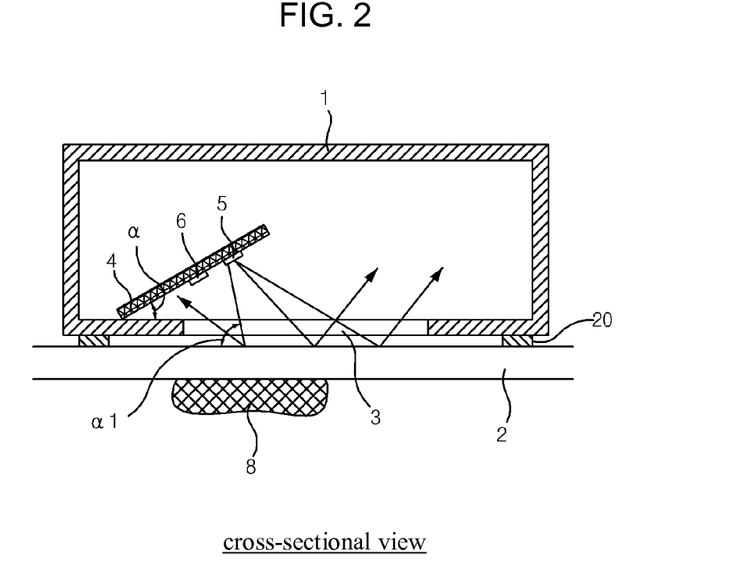
FIG. 2 is a conceptual illustration showing the light reflection process of the light source, which is a major element of the present invention, at the surface of the windshield.
Figure 4:
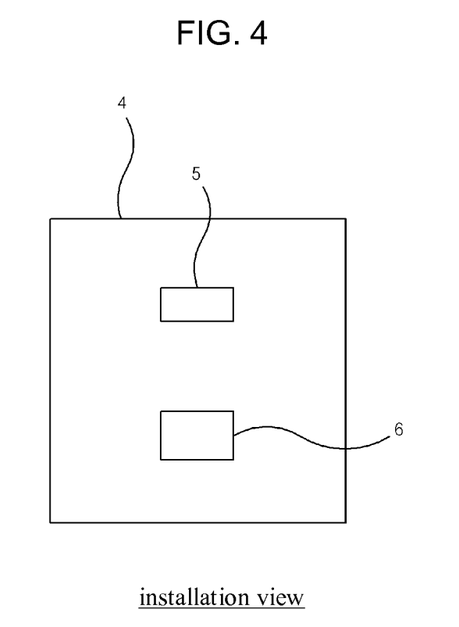
FIG. 4 is a conceptual illustration showing the first exemplary embodiment of an arrangement of a light source and a light receiving element which are major elements of the present invention.
Figure 5:
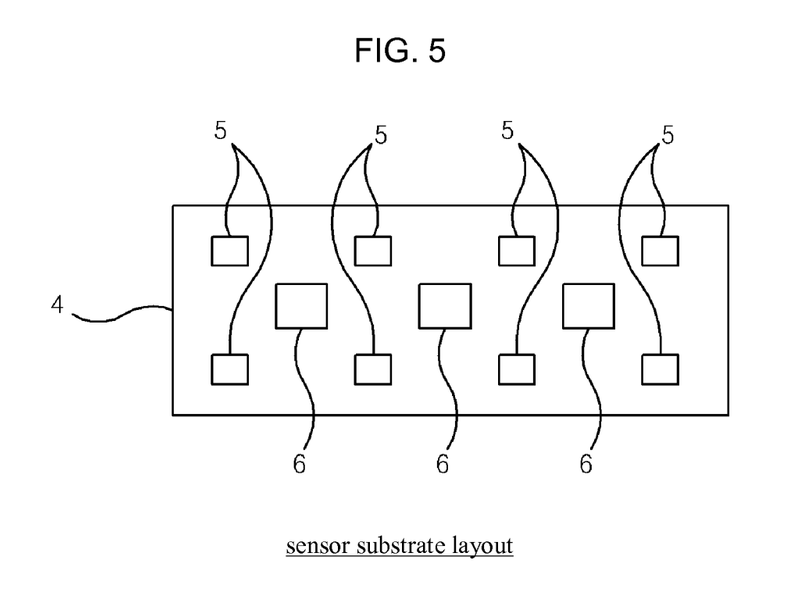
FIG. 5 is a conceptual illustration showing the second exemplary embodiment of an arrangement of light sources and light receiving elements which are major elements of the present invention.
Figure 6:
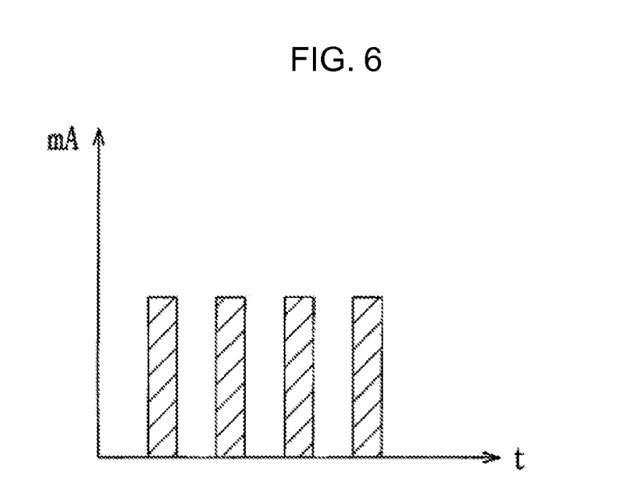
FIG. 6 is a graph showing a pulse signal of the light source which is a major element of the present invention.

FIG. 1 is a conceptual illustration showing a rain sensor of the present invention installed on the windshield; FIG. 2 is a conceptual illustration showing the light reflection process of the light source, which is a major element of the present invention, at the surface of the windshield; FIG. 3 is a conceptual illustration showing the light reflection process of the light source, which is a major element of the present invention, at a raindrop; FIG. 4 is a conceptual illustration showing the first exemplary embodiment of an arrangement of a light source and a light receiving element which are major elements of the present invention; FIG. 5 is a conceptual illustration showing the second exemplary embodiment of an arrangement of light sources and light receiving elements which are major elements of the present invention; FIG. 6 is a graph showing a pulse signal of the light source which is a major element of the present invention; and FIG. 7 shows a conceptual illustration of a signal sensing process and an ambient light reduction method of the present invention.

According to the present invention of FIG. 1 to FIG. 7, the substrate (4) where the light sources (5) and the light receiving elements (6) are mounted is installed inside of the housing (1), and the substrate (4) where the light sources (5) and the light receiving elements (6) are mounted is installed inclining with respect to the windshield (2).

The housing (1) is comprised of a roughly rectangular shape box having an opening (3) formed on the surface facing the windshield (2), and double coated adhesive tapes (20) are prepared at the exterior surface of the opening (3) so that the housing is attached on the windshield (2) by the double coated adhesive tapes (20).

A substrate (4) where the light sources (5) and the light receiving elements (6) are mounted is installed inside of the housing (1). At this time, the substrate (4) is arranged inclining with respect to the opening (3) of the housing (1) using a support (7) (shown in FIG. 3) such as a bracket so that the light source (5) and the light receiving elements (6) are installed inclining with respect to the surface of the windshield (2). The slanted angle of the substrate (4) with respect to the surface of the windshield (2) is an acute angle not exceeding 90 degrees.

At this time, it is a remarkable that an infrared LED is adopted as a light source (5) while an infrared sensor is adopted as a light receiving element (6), and such features will be described later.

According to the above described configuration of the present invention, an infrared signal light radiated from the infrared LED used as a light source (5) during rain passes through the opening (3) of the housing (1) and the windshield (2) and a part of the signal light is reflected back from the raindrop (8) fallen on the windshield (2) and again passes through the windshield (2) and photoelectrically transduced in the light receiving element (6) near the LED which is the light source (5); this photoelectrically transduced electrical signal is reformed as a signal in the receiver (9), and an operation signal of the wipers on the windshield (2) is generated in accordance with the received signal by comparing with the pre-inputted look-up table. The amplitude of the signal light generated through above described process determines the correct operation frequency of the wipers on the windshield (2) in the microcomputer (10) in accordance with the pre-inputted look-up table.

At this time, the substrate (4) where the light receiving element (6) and the light source (5) are mounted is arranged inclining with respect to the windshield (2); therefore when the light being emitted from the light source (5) enters into the windshield (2), the reflected light from the surface of the windshield (2) is not received by the light receiving element (6) but exits outside; the light entered into the windshield (2) refracts at a certain angle due to the difference in density, and the refracted light becomes extinct outside of the windshield (2); meanwhile the light transmitted through the windshield (2) passes through the raindrop (8) and refracted at a certain angle and scattered at the outer surface of the raindrop (8); only the scattered light from the raindrop (8) is received by the light receiving element (6) so that the effect of the light reflected from the surface of the windshield (2) is minimized, hence the degradation in the SNR due to the effect of reflected light from the surface of the windshield (8) except the reflected light from the raindrop (8) is prevented effectively; it implies that the expected performance in terms of efficiency in raindrop (8) sensing can be achieved therefore a sufficient efficiency can be obtained by precise control of the alternating speed of the wipers of a vehicle. In other words, the present invention is very efficient in enhancing the performance in raindrop (8) sensing by receiving only the scattered light from the raindrop (8) while minimizing the amount of the direct reflection from the surface of the windshield (2).

In summary, the most significant feature of the present invention is that the raindrop sensing efficiency can be enhanced by receiving only the signal light reflected from the raindrop (8) itself while minimizing the effect of the reflected light from the surface of the windshield (2) by arranging the substrate (4), where the light source (5) and the light receiving element (6) are mounted, inclining with respect to the surface of the windshield (2).

As shown in FIGS. 2 and 3, the light from the light source (5) is radiated in a gradually expanding shape; the radiation angle is adjusted such that the light among the radiating light from the light source (5) directing towards the light receiving element (6) forms an acute angle (i.e., less than 90 degrees) with respect to the windshield (2).

Therefore the light reflected directly from the surface of the windshield (2) exits outside of the receiving area of the light receiving element (6) so as to minimize the amount of light received by the light receiving element (6) caused by the reflection from the windshield (2), hence only the amount of light reflected from the raindrop (8) is received by the light receiving element (6) so that only the signal scattering from the raindrop (8) is detected.

At this time, since the double coated adhesive tapes (20) prepared at the exterior surface of the opening (3) of the housing (1), so the housing (1) where the substrate (4) having the light receiving element (6) and the light source (5) installed thereon can be quickly and easily attached and detached to and from the surface of the windshield (2) by the double coated adhesive tapes (20).

Meanwhile, the configuration of the present invention adopts arrangement where multiple light sources (5) are disposed along the top, bottom, left, and right directions with respect to the light receiving element (6) in a lattice-like pattern as shown in FIG. 5. To be more specific, multiple light sources (5) are arranged in a lattice-like pattern along the top, bottom, left, and right directions with respect to the light receiving element (6).

Since one light receiving element (6) is surrounded by four LEDs that are used as light sources in the configuration of the first unit sensing area, one light receiving element (6) includes four light paths, hence it is economical in terms of required number of light receiving elements (6), and brings on expansion effect in raindrop (8) sensing area.

Furthermore, the sensing area can be expanded by adding two light sources (5) and one light receiving element (6) to the first unit sensing area (ie, sensing area comprised of one light receiving element (6) and four light sources (5)) therefore since same effect of using four LEDs as in the first unit sensing area by adding two LEDs and one light receiving element (6) to a neighboring sensing area, it has an advantage in that the number of elements can be reduced while expanding sensing area.

It is also a special feature of the present invention that the light source (5) is comprised of an infrared LED and the light receiving element (6) is comprised of an infrared sensor. In other words, an infrared light having a longer wavelength than a visible light is a non-visible light, and an infrared LED used as a light source (5) emits infrared light several tens of times stronger than the ambient light, and the infrared sensor used as a light receiving element (6) receives only non-visible light so that it does not receive the other person's headlights entering through the wiper movements during night driving in rain but it receives only the non-visible light emitted from the LED and reflect from the raindrop so the efficient operation immune to ambient light is achieved. In other words, since the infrared LED does not emit visible light and the infrared sensor used as a light receiving element (6) does not receive visible light, the light signal from the other person's vehicle caused by the alternating movement of the wipers is excluded, therefore it has an effect of preventing the possible operation error etc.

Since the interior of the housing (1) is colored black to absorb light and the surface-treated for diffuse reflection, most of the reflected light from the surface of the windshield (2) is diminished due to the black color of the interior where the light receiving element (6) is mounted and surface-treated for diffuse reflection, therefore the effect of the reflected light other than that from the raindrop (8) can be certainly reduced.

At this time, as shown in FIG. 6, the infrared LED used as a light source (5) is designed to generate a pulsed light signal and generates a series of pulsed light signals having peak current of a few hundred milliamperes (mA); and the light receiving element (6) is designed to have a time delay so as not to respond to the light signals having short pulse widths therefore enhancement in the sensing efficiency can be expected. In other words, the time delay is applied so as not to respond to the light signals having short pulse widths occurring instantaneously when the wipers are operated therefore the sensing efficiency can be enhanced for sure.

FIG. 7 shows an ambient light reduction method of the present invention, the light source (5) emits a signal light in accordance with the signal generated in the transmitter (11). The transmitter (11) of the present invention is comprised of an oscillator (13) oscillating a square wave between 10 KHz and 100 KHz frequency range, a modulator (14) modulating the infrared LED light source (5) according to the oscillated signal; the receiver (9) is comprised of an amplifier (15) amplifying the photoelectrically transduced electrical signal from the light receiving element (6) and a band pass filter (16) filtering out frequency components identical to the oscillating frequency of the oscillator (13).

The oscillator (13) oscillates a square wave between 10 KHz and 100 KHz frequency range and the modulator (14) modulates the LED(5) optically in accordance with the oscillating signal. Thus generated signal light is reflected from the raindrop (2) fallen on the windshield (2) and received by the light receiving element (6). The electrical signal photoelectrically transduced in the light receiving element (6) is amplified in the amplifier (15), then only the frequency components identical to the oscillation frequency of the oscillator (13) are filtered out in the band pass filter (16). A correct operation frequency of the wiper is determined in the microcomputer (10) using the pre-inputted look-up table according to the amplitude of the generated signal light and the result is outputted thereby the wipers are operated in response to the level of rainfall.

[Industrial Applicability]

The present invention can be used as a rain sensor having a simplified optical system for an easy installment, and capable of preventing degradation in the SNR affected by the light reflected from the surface of the windshield except from the raindrops by installing the light source transmitting light into the windshield and the light receiving element collecting reflected light from the raindrops inclined with respect to the surface of the windshield, and designed to exclude optical signals caused by the alternating motion of the wipers so that the effect from the headlights of another person's vehicle during the operation of the wipers is prevented so as to enhance operation reliability significantly

The invention claimed is:

1. A rain sensor for detecting rainfall during rain comprising:
    a light source (5) radiating signal light according to a generated signal in a transmitter (11);
    a light receiving element (6), located in a unit sensing area and arranged with surrounding four light sources (5), for receiving light and facing towards a reflected light from raindrops caused by the radiated light of the light sources (5);
    an infrared filter installed in an opening formed at one side of a housing (1) of the rain sensor; and
    a receiver (9) excluding noise components caused by a reflection from a surface of a windshield (2) and extracting only a modulated frequency component of an optical signal to determine the amount of existing raindrops on the surface of the windshield so as to minimize an effect of ambient light and enhance a raindrop sensing probability
    wherein the light receiving element directly receives the reflected light, and
    wherein the light source (5) and the light receiving element (6) are mounted on a substrate (4), and the substrate (4) is inclined with respect to the surface of the windshield (2) such that the light source (5) the light receiving element (6) are inclined with respect to the surface of the windshield (2), and the light source (5) and the light receiving element (6) are disposed serially along a same direction.

2. The rain sensor for detecting rainfall during rain of claim 1, wherein the sensing area can be expanded by adding two light sources (5) and one light receiving element (6) in a lattice-like pattern to the left-right or top-bottom side of the unit sensing area comprising a light receiving element (6) surrounded by four light sources (5) for receiving light and facing towards the reflected light from the raindrops caused by the radiated light of the light sources (5).

3. The rain sensor for detecting rainfall during rain of claim 1, wherein the light sources (5) are infrared LEDs and arranged with the light receiving element (6) in a lattice-like pattern.

4. The rain sensor for detecting rainfall during rain of claim 1, wherein the interior of the housing (1) of the raindrop sensing device is colored black to absorb light and surface-treated for diffuse reflection.

5. The rain sensor for detecting rainfall during rain of claim 1, wherein the transmitter (11) is comprised of an oscillator (13) oscillating a square wave between 10 KHz and 100 KHz frequency range and a modulator (14) modulating the infrared LED light source (5) according to the oscillated signal.

6. The rain sensor for detecting rainfall during rain of claim 5, wherein the receiver (9) is comprised of an amplifier (15) amplifying the photoelectrically transduced electrical signal from the light receiving element (6) and a band pass filter (16) filtering out frequency components identical to the oscillating frequency of the oscillator (13).

7. The rain sensor for detecting rainfall during rain of claim 6, wherein the infrared filter installed on the front surface of the light receiving element (6) suppresses reception of external visible light frequencies except the optical signal.

8. The rain sensor for detecting rainfall during rain in claim 1, wherein the receiver (9) transfers information to a microcomputer (10) according to the amplitude of the signal light, then the microcomputer (10) determines the appropriate operation frequency of the wipers according to the pre-inputted look-up table and outputs a raindrop sensing signal (12).

9. A rain sensor for detecting rainfall during rain comprising:
    a light source (5) radiating light into a windshield (2);
    a light receiving element (6) performing photoelectric transduction by sensing an optical signal when the radiated light from the light source (5) is reflected from raindrops fallen on the windshield (2); and a receiver (9) judging a level of rainfall by receiving a photoelectrically transduced signal of the light receiving element (6)

wherein the light source (5) and the light receiving element (6) are inclined with respect to a surface of the windshield (2) such that the light from the light source (5) reflected directly from the surface of the windshield (2) exits outside of the light receiving element (6), and only the reflected light from the raindrops fallen on the windshield (2) is received so as to operate wipers, and wherein the light source (5) and the light receiving element (6) are mounted on a substrate (4), and the substrate (4) is inclined with respect to the surface of the windshield (2) such that the light source (5) the light receiving element (6) are inclined with respect to the surface of the windshield (2), and the light source (5) and the light receiving element (6) are disposed serially along a same direction.

10. The rain sensor for detecting rainfall during rain of claim 9, wherein a plurality of light sources (5) is arranged at the top, bottom, left, and right side of the light receiving element (6) in a lattice-like pattern.

11. The rain sensor for detecting rainfall during rain of claim 10, wherein the sensing area can be expanded by disposing two additional light sources (5) and one light receiving element (6) at the top-bottom or left-right direction of a unit sensing area where a plurality of light sources (5) are disposed at the top, bottom, left, and right side of the receiving element (6) in a lattice-like pattern.

12. The rain sensor for detecting rainfall during rain of claim 9, wherein the light source (5) is comprised of an infrared LED and the light receiving element (6) is comprised of an infrared sensor.

13. The rain sensor for detecting rainfall during rain of claim 9, wherein the housing (1) is installed on the windshield (2) where the light of the light source (5) is being radiated so that the front opening (3) and the windshield are facing each other, and the substrate (4) where the light sources (5) and the light receiving elements (6) are mounted is installed inside of the housing (1), and the substrate (4) where the light sources (5) and the light receiving elements (6) are mounted is installed inclining with respect to the windshield (2), and the interior of the housing (i) is surface-treated for diffuse reflection to absorb light.

14. The rain sensor for detecting rainfall during rain of claim 13, wherein the infrared LED used as a light source (5) is designed to generate a pulsed light signal and the light receiving element (6) is designed to have a time delay so as not to respond to the ambient light signals having short pulse widths which do not match with the pulsed signal of the light source (5).

15. The rain sensor for detecting rainfall during rain of claim 9, wherein the light source (5) is configured to transmit a signal light according to the signal generated in the transmitter (11), and the transmitter (11) is comprised of an oscillator (13) oscillating a square wave between 10 KHz and 100 KHz frequency range and a modulator (14) modulating the infrared LED light source (5) according to the oscillated signal.

16. The rain sensor for detecting rainfall during rain of claim 15, wherein the receiver (9) is comprised of an amplifier (15) amplifying the photoelectrically transduced electrical signal from the light receiving element (6) and a band pass filter (16) filtering out frequency components identical to the oscillating frequency of the oscillator (13).

* * * * *